(12) United States Patent
Biedermann (10) Patent No.: US 9,055,980 B2
(45) Date of Patent: Jun. 16, 2015

(54) BONE ANCHORING DEVICE

(75) Inventor: Markku Biedermann, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 25 days.

(21) Appl. No.: 12/845,551

(22) Filed: Jul. 28, 2010

(65) Prior Publication Data

US 2011/0034957 A1 Feb. 10, 2011

Related U.S. Application Data

(60) Provisional application No. 61/229,061, filed on Jul. 28, 2009.

(30) Foreign Application Priority Data

Jul. 28, 2009 (EP) ..................................... 09166639

(51) Int. Cl.
*A61B 17/56* (2006.01)
*A61B 17/70* (2006.01)

(52) U.S. Cl.
CPC ......... *A61B 17/7035* (2013.01); *A61B 17/7032* (2013.01); *A61B 17/7041* (2013.01)

(58) Field of Classification Search
CPC ............... A61B 17/70; A61B 17/7001; A61B 17/7032; A61B 17/7034; A61B 17/7035; A61B 17/7041
USPC ........................... 606/246, 305–308, 250–275
See application file for complete search history.

(56) References Cited

U.S. PATENT DOCUMENTS

| | | | |
|---|---|---|---|
| 5,254,118 A | * | 10/1993 | Mirkovic ....................... 606/264 |
| 5,501,684 A | | 3/1996 | Schlapfer et al. |
| 6,063,090 A | | 5/2000 | Schläpfer |
| 6,187,005 B1 | | 2/2001 | Brace et al. |
| 6,290,703 B1 | | 9/2001 | Ganem |

(Continued)

FOREIGN PATENT DOCUMENTS

| | | |
|---|---|---|
| EP | 0 553 424 | 8/1993 |
| JP | 05-269143 | 10/1993 |

(Continued)

OTHER PUBLICATIONS

European Search Report for priority application No. EP 09 16 6639 dated Nov. 30, 2009, 7 sheets.

*Primary Examiner* — Christian Sevilla
*Assistant Examiner* — Eric S Gibson
(74) *Attorney, Agent, or Firm* — Christie, Parker & Hale, LLP (57) ABSTRACT

A bone anchoring device includes a bone anchoring element having a shank and a head, a continuous one-piece receiver member, a continuous one-piece first locking element and a second locking element. The receiver member has a first chamber for receiving the head, the head being pivotable in the first chamber, and a second chamber with a channel for receiving the rod. A first locking element fixes the head in the first chamber at an angle, and a second locking element fixes the rod in the second chamber. The receiver member includes a body including both the first chamber and the second chamber. The head and the rod can be inserted and locked independently from each other. The head is fixed by exerting pressure onto it. The bone anchoring device is particularly applicable to the stabilization of the spine in the sacro-iliac and the cervical region.

19 Claims, 8 Drawing Sheets

(56) References Cited

U.S. PATENT DOCUMENTS

| | | | |
|---|---|---|---|
| 6,309,390 B1 | 10/2001 | Le Couedic et al. | |
| 6,520,963 B1 | 2/2003 | McKinley | |
| 6,676,661 B1* | 1/2004 | Martin Benlloch et al. | 606/264 |
| 6,685,705 B1* | 2/2004 | Taylor | 606/278 |
| 7,166,109 B2 | 1/2007 | Biedermann et al. | |
| 7,186,255 B2* | 3/2007 | Baynham et al. | 606/266 |
| 8,057,518 B2* | 11/2011 | Frasier et al. | 606/267 |
| 8,062,339 B2* | 11/2011 | Hammer et al. | 606/264 |
| 8,641,737 B2* | 2/2014 | Matthis et al. | 606/265 |
| 2003/0073996 A1 | 4/2003 | Doubler et al. | |
| 2003/0100896 A1 | 5/2003 | Biedermann et al. | |
| 2004/0039388 A1 | 2/2004 | Biedermann et al. | |
| 2004/0111088 A1* | 6/2004 | Picetti et al. | 606/61 |
| 2005/0070899 A1 | 3/2005 | Doubler et al. | |
| 2006/0079898 A1* | 4/2006 | Ainsworth et al. | 606/61 |
| 2006/0235389 A1* | 10/2006 | Albert et al. | 606/61 |
| 2006/0235392 A1* | 10/2006 | Hammer et al. | 606/61 |
| 2007/0161995 A1 | 7/2007 | Trautwein et al. | |
| 2007/0265621 A1 | 11/2007 | Matthis et al. | |
| 2007/0288004 A1 | 12/2007 | Alvarez | |
| 2008/0147129 A1 | 6/2008 | Biedermann et al. | |
| 2008/0195122 A1 | 8/2008 | Castellvi et al. | |
| 2009/0036929 A1 | 2/2009 | Reglos et al. | |
| 2009/0062861 A1* | 3/2009 | Frasier et al. | 606/278 |
| 2009/0287254 A1* | 11/2009 | Nayet et al. | 606/278 |

FOREIGN PATENT DOCUMENTS

| | | |
|---|---|---|
| JP | 2007-319664 A | 12/2007 |
| JP | 2008-534075 A | 8/2008 |
| WO | WO 94/00066 | 1/1994 |
| WO | WO 2005/058173 A1 | 6/2005 |
| WO | WO 2006/104874 A2 | 10/2006 |
| WO | WO 2008/098201 A2 | 8/2008 |
| WO | WO 2009/011929 A1 | 1/2009 |

* cited by examiner

BONE ANCHORING DEVICE

CROSS-REFERENCE TO RELATED APPLICATION(S)

This present application claims the benefit of U.S. Provisional Patent Application No. 61/229,061, filed Jul. 28, 2009, and claims priority from European Patent Application EP 09 166 639.6, filed Jul. 28, 2009, the disclosures of which are incorporated herein by reference.

BACKGROUND

The invention relates to a bone anchoring device with a bone anchoring element having a shank and a head and a receiver member for receiving the head and for receiving a rod. The bone anchoring element is pivotable in the receiver member and can be locked by a first locking element. The rod can be locked by a second locking element which is separated and independent from the first locking element. The bone anchoring device is particularly applicable for the stabilization of the cervical or the lumbosacral region of the spinal column.

Figures 1, 2, 3:
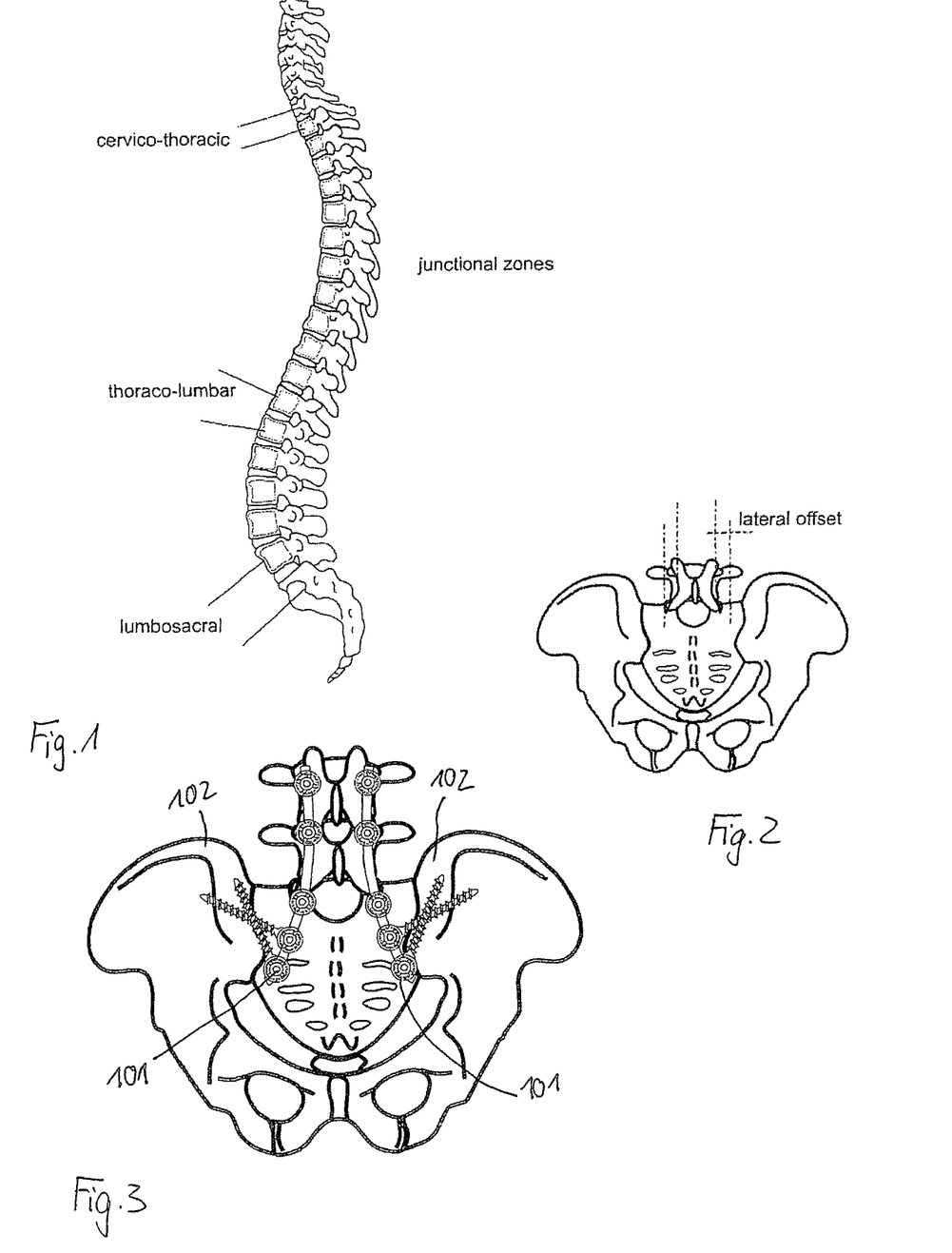
FIG. 1 shows a schematic side view of the spinal column with indication of particular regions of the spinal column and particular regions with difficult junctional zones.
FIG. 2 shows a schematic rear view of the lumbosacral region of the spine.
FIG. 3 shows a stabilization of the spinal column in the lumbosacral region.

FIG. 1 shows different zones of the spinal column in a side view. In FIG. 2 the lumbosacral region is shown in a posterior view. In this region, it can be advantageous to arrange the stabilization rod offset from the anchoring elements. As depicted in FIG. 3, in the stabilization of the iliosacral bones, polyaxial screws 101 with a shank are used that extend at an angle of approximately 90° out of a plane containing the rod axis and a central axis of the receiver member to allow them to be anchored laterally in the ilium 102. A lateral offset is also helpful in all other junctional zones of the spine.

Polyaxial bone screws are known in which the rod is arranged above of the head of the bone anchoring element. Usually these polyaxial bone screws have a pressure element which is located between the rod and the head. A locking element, such as a set screw, presses onto the rod that itself presses onto the pressure element to simultaneously lock the head and the rod in their positions. US 2003/0100896 A1 describes a specific example of a polyaxial bone screw that allows the independent fixation of the head and the rod. To accomplish this, a dual part locking element is used, one part of which presses onto the pressure element for fixation of the head and the other part presses onto the rod for fixing the rod. The first and the second locking element are not independent from each other.

Although the known examples of polyaxial screws are suitable for stabilizing the spine in most of the clinical applications, there is still the need of having a polyaxial screw for specific applications that require the rod to be guided laterally from the screw or the screw extending in a direction out of a plane containing the rod axis.

US 2007/0265621 describes a polyaxial bone screw that is applicable in particular to the stabilization of the sacrum.

WO 94/00066 describes an osteosynthetic fixation device that consists of a bone screw having a conical head section and a spherical slotted clamping component that receives the conical head section and that is pivotable in a spherical segment-shaped bore of a connection element. The connection element has a channel for introducing a stabilization rod, and the channel for the rod is provided laterally from the bore that receives the bone screw. Since the clamping component is expanded by the conical head section of the bone screw, it is necessary to have a tension element that draws the conical head section into the clamping element. Therefore, on top of the conical head section of the bone, screw sufficient space must be provided for the tension element.

U.S. Pat. No. 6,290,703 B1 describes a bone fixing device in particular for fixing to the sacrum for osteosynthesis of the backbone. The device comprises an elongate link that receives at least one bone-fastening screw that passes through an orifice formed in the link. In the bottom of the link there is a bearing surface of essentially circular cross-section. The head of the screw includes an essentially spherical surface for bearing against the bearing surface. The device further includes a plug suitable for coming into clamping contact against said screw head to hold it in a desired angular position.

U.S. Pat. No. 7,166,109 B2 describes a bone anchoring device comprising a bone screw and a receiver member with a lateral channel for the rod. The receiver member is a two-part receiver member. The device has a low profile and is particularly applicable to the stabilization of the pelvis.

It is the object of the invention to provide a bone anchoring device that is suitable for many purposes including specific applications such as stabilization of the cervical spine and the sacro-iliac region of the spine.

SUMMARY

The object is solved by a bone anchoring device according to claim 1. Further developments are given in the dependent claims.

The bone anchoring device according to the invention has the advantage that the rod and the bone anchoring element can be locked independently from each other with independent locking elements. The locking of the head is possible, for example, by using a single set screw that engages in a standard thread of the head receiving chamber. Since the receiver member is fully threaded, no spreading of the flanks occurs. Therefore, the head can be safely locked with a simple one-part element. Since the locking of the rod and the locking of the bone anchoring element are completely independent, the rod and the bone anchoring element can be locked and unlocked again independently of each other. This allows easy and precise adjustment of the head and the rod.

The bone anchoring device has a lower profile than the standard polyaxial screws. The profile is similar in size to a monoaxial screw that has only the receiver, the rod and the locking element.

Different receiver members can be provided with different orientations of the rod with respect to the bone anchoring element. Therefore, a set of different receivers can be provided to allow the surgeon to select the suitable arrangement. In particular, it is possible to select the lateral offset of the rod with respect to the bone anchoring element. Since the head of the bone anchoring element is easily locked by a simple one-part locking element, the bone anchoring device can be assembled by hand and needs not to be pre-assembled by the manufacturer. This allows the surgeon to select a suitable screw shank and combine it with the receiver member.

Since all existing screw shanks with heads can be used, the system has an enhanced modularity.

Further features and advantages of the invention will become apparent from the followed detailed description of embodiments of the invention by means of the accompanying drawings. In the drawings:

BRIEF DESCRIPTION OF THE DRAWINGS

FIG. 12b is a perspective view from the bottom of the modified example shown in FIG. 12a.

DETAILED DESCRIPTION

The bone anchoring device 1 according to a first embodiment shown in FIGS. 4 to 12 includes a bone anchoring element, in this case a screw member 2 having a threaded shaft 3 having a bone thread and a head 4. The head 4 is shaped, for example, as a spherical segment. It has a recess 4' at its free end for engagement with a screwing-in tool. The bone anchoring device further includes a receiver member 5 for connecting the screw member 2 to a rod 20. The receiver member 5 includes two portions in the form of separated chambers, a head receiving chamber 6 and a rod receiving chamber 7. The head receiving chamber 6 and the rod receiving chamber 7 are connected by means of an intermediate portion 8, which is in the embodiment shown a rod portion or a bar. The head receiving chamber 6 is, as shown in FIGS. 4 to 6 and FIG. 8, a body with a substantially cuboid shape having a first end 6a and an opposite second end 6b. A through-hole 9 extends from the first end to the second end. In a region adjacent to the second end, the diameter of the through-hole is smaller than that adjacent to the first end. Thus, a seat 9a is provided for the screw head 4, preventing escaping of the screw head and enabling the screw head 4 to pivot within the head receiving chamber 6. The seat can have a spherical or a tapered portion or a portion with any other shape. Adjacent to or near the first end 6a, an internal thread 10 is provided. The internal thread can be a metric thread or can have any other thread shape. Since the thread is provided in the through-hole, the thread is closed in a circumferential direction. This allows use of a metric thread since a splaying of a U-shaped receiver, as it is known to be a problem in conventional polyaxial bone screws, does not occur. The diameter of the opening at the second end 6b, which is defined by the through-hole, is such that the shank 3 of the screw member can be passed therethrough. When the head 4 of the screw member 2 is in the head receiving portion, the screw member can pivot so that the shank axis can assume different angles with respect to the axis of the through-hole.

Figure 9:
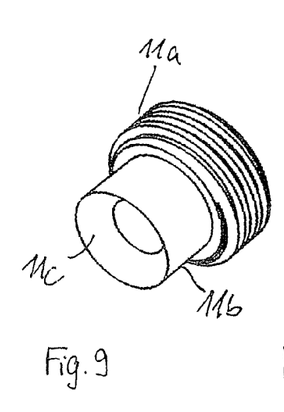
FIG. 9 is a perspective view of the locking element for locking the head.
Figure 10:
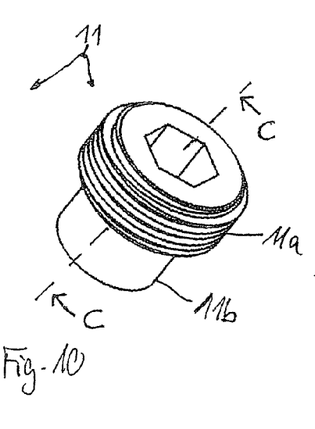
FIG. 10 is another perspective view of the locking element of FIG. 9.
Figure 11:
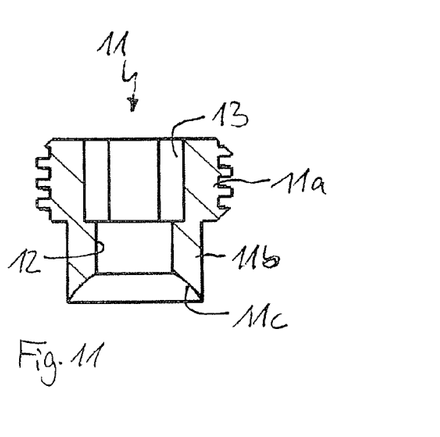
FIG. 11 is a sectional view of the locking element of FIGS. 9 and 10, the section being taken along line C-C in FIG. 10.

To fix the angular position of the screw member 2 in the head receiving chamber 6, a first locking element 11 is provided, which can be seen in detail in FIGS. 9 to 11. The first locking element 11 has a threaded portion 11a with an external thread cooperating with the internal thread 10 of the through-hole, and a cylindrical portion 11b, which extends in the direction of the head 4 when the screw member and the first locking element are inserted into the head receiving chamber. The threaded portion 11a and the cylindrical portion 11b form a one-part first locking element 11. At the free end of the cylindrical portion 11b, a spherical recess 11c is formed, the radius of which is adapted to the radius of the head 4. The recess 11c serves to distribute the load exerted by the first locking element 11 onto the head 4. The outer diameter of the cylindrical portion 11b is slightly smaller than the inner diameter of the through-hole 9 and also of the threaded portion 11a so that the first locking element can be easily introduced into the through-hole. The first locking element 11 further comprises a coaxial bore 12 that allows access to the screw head 4 by a tool. At the free end of the threaded portion 11a, the first locking element 11 has a structure, such as a hexagonal structure 13 for engagement with a tool.

Figure 4:
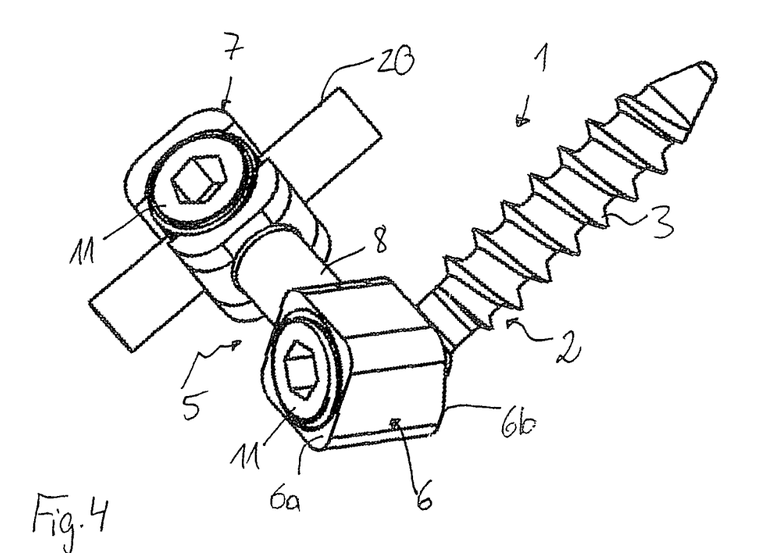
FIG. 4 shows a perspective view of a first embodiment of the bone anchoring device in an assembled state.
Figure 5:
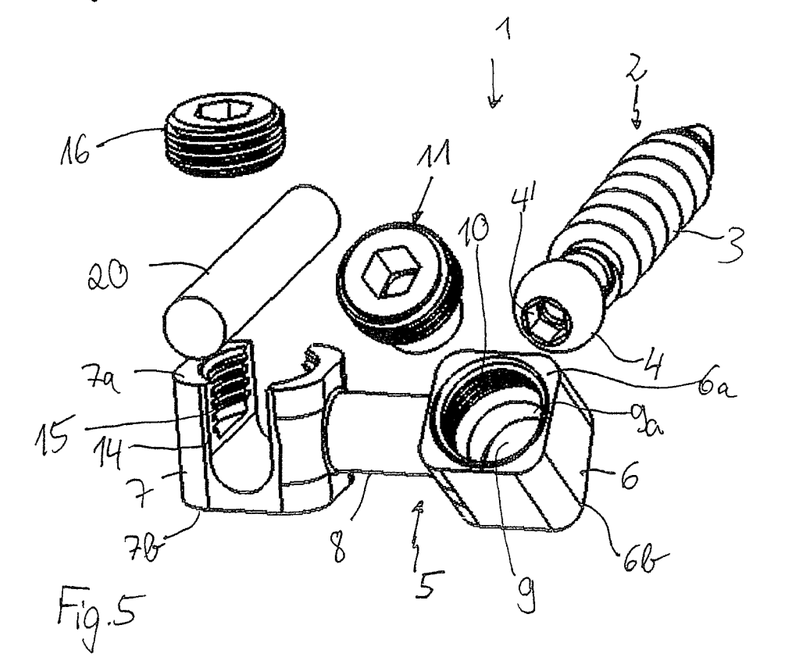
FIG. 5 shows a perspective exploded view of the bone anchoring device of FIG. 4.
Figures 6, 7, 8:
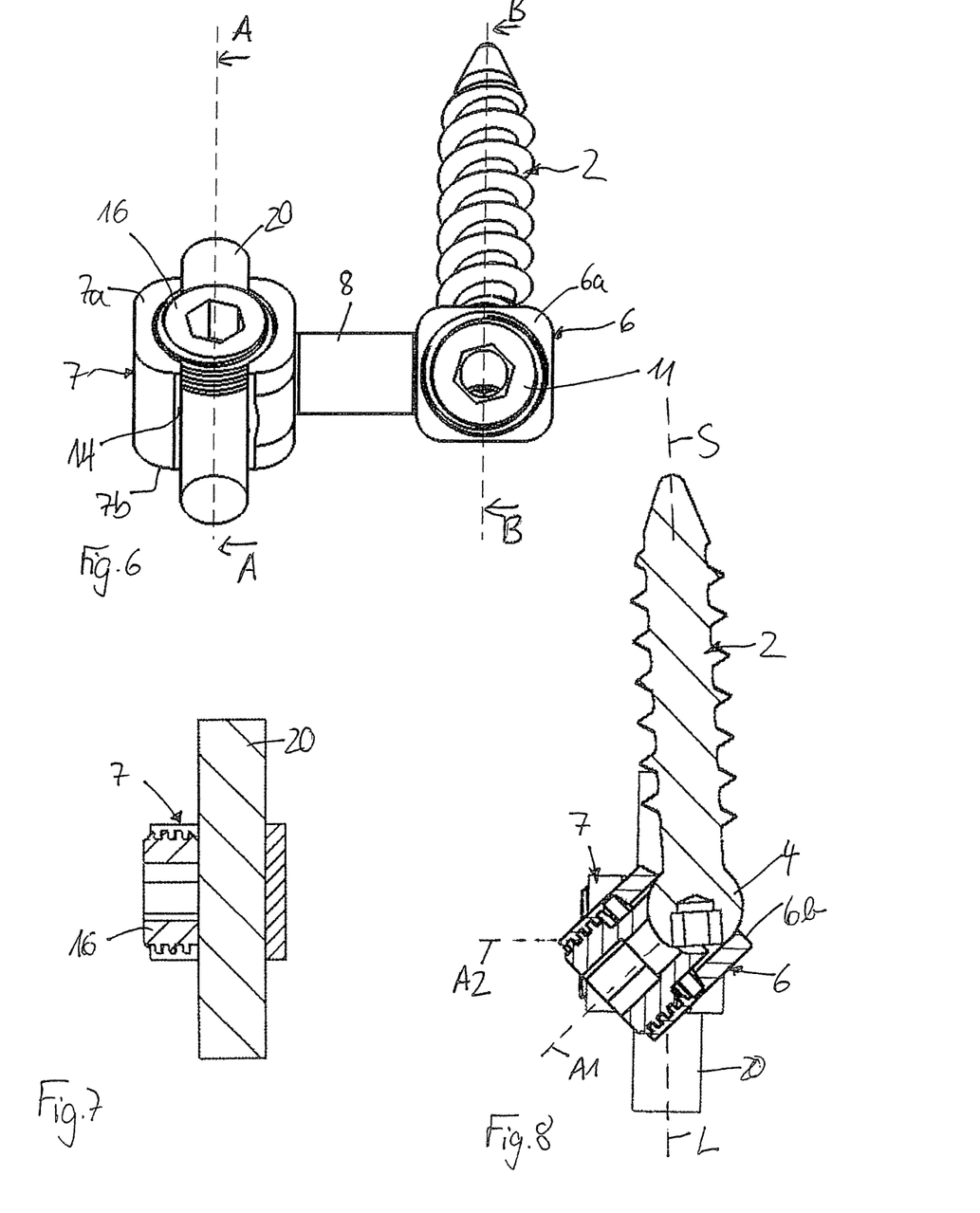
FIG. 6 shows another perspective view of the bone anchoring device of FIG. 4.
FIG. 7 shows a sectional view of the rod receiving portion of the bone anchoring device of FIG. 6, the section being taken along line A-A in FIG. 6.
FIG. 8 is a sectional view of the head receiving portion of the bone anchoring device according to FIG. 6, the section being taken along line B-B in FIG. 6.

Referring to FIGS. 4 and 8, the second end 6b of the head receiving chamber 6 has an inclined surface that extends at an angle to the surface defined by the first end 6a. By means of this, the pivot angle of the screw member can be enlarged to one side.

As can be seen in FIGS. 4 to 7, the rod receiving chamber 7 has also a cuboid shape with a first end 7a and an opposite second end 7b. A U-shaped recess 14 extends from the first end 7a in the direction of the second end 7b to form a channel for the rod 20 to be received therein. By means of the U-shaped recess 14, two free legs are formed. An internal thread 15 extends from the first end or near the first end 7a in the direction of the second end 7b for screwing in a second locking element 16. The second locking element 16 is in this embodiment a set screw. The internal thread 15 can be a flat thread with horizontal flanks to eliminate a splaying of the legs when the second locking element 16 is screwed in.

In the embodiment shown in FIGS. 4 to 12, the head receiving chamber 6 and the rod receiving chamber 7 are connected by the intermediate portion 8 and arranged in such a way that the central axis A1 of the through-hole of the head receiving chamber 6 is inclined by an angle of 45° with respect to the central axis A2 of the rod receiving chamber 7, as can be seen in particular in FIG. 8. The arrangement of the chambers 6, 7 with respect to each other is such that the internal threads of the through-hole and the U-shaped recess, respectively, are oriented towards the same side. By means of this arrangement, as can be seen in FIG. 8, it is possible to align the screw axis S nearly parallel to the longitudinal axis L of the rod. By means of the length of the intermediate portion 8, the lateral offset between the screw and the rod can be defined.

The shape of the head receiving chamber 6 and the rod receiving chamber 7 is not limited to the cuboid shape shown, it is also possible to use a cube shape, a cylindrical shape or any other symmetric or asymmetric shape. Although the head receiving chamber 6 is shown to be a top loading chamber, where the screw is inserted with its tip portion first through the first end 6a, it can also be designed as a bottom loading chamber where the head is introduced from the bottom, i.e. the second end 6b.

The material of the elements of the bone anchoring device is a body-compatible material, such as stainless steel, titanium, and body-compatible alloys such as nickel-titanium alloys, for example nitinol. It is also possible to construct the bone anchoring device or parts thereof from a body-compatible plastic material, such as, for example medical-grade PEEK.

In modifications of this embodiment, the receiver member can be constructed such that the head receiving chamber 6 and the rod receiving chamber 7 have another orientation with respect to each other. Any orientation is possible, for example, an orientation where the central axes A1 and A2 are parallel to each other.

Figure 12A:
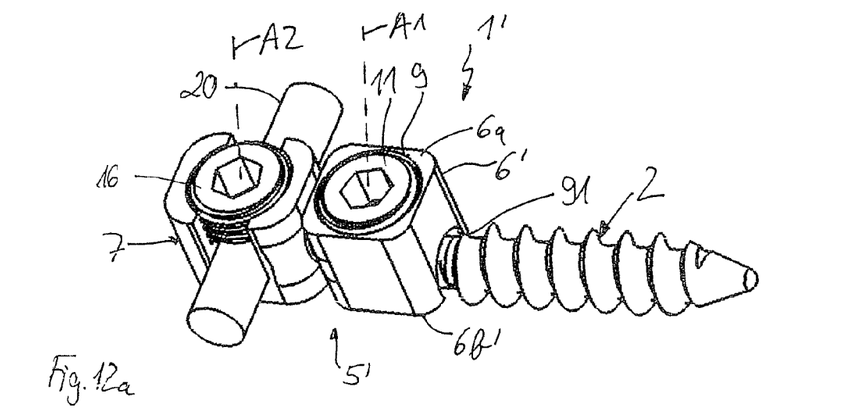
FIG. 12a is a perspective view from the top of a modified example of the first embodiment in an assembled state.
Figure 12B:
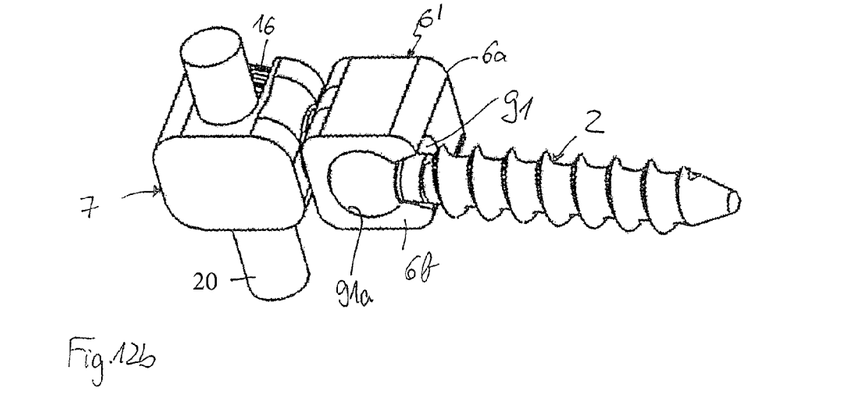

A specific modification of the bone anchoring device according to the first embodiment is shown in FIGS. 12a and 12b. Like parts are indicated with the same reference numerals as in the first embodiment and the descriptions thereof are not repeated. The bone anchoring device 1' of this modified embodiment has an identical rod receiving chamber 7 and a modified head receiving chamber 6'. The head receiving chamber 6' has a through-hole 9 in which the first locking element 11 is screwed in and a seat 91a for the head 4 provided at the second end, which is sized such that the head is pivotably held therein. It further includes a recess 91, which extends in the region near the second end 6b' perpendicular to the through-hole 9 and is open to the second end 6b' and to the through-hole 9. When the screw member is inserted into the through-hole 9 it can be pivoted once the head 4 is in the seat 91a such that the threaded shank extends at an angle of around 90° to the through-hole 9. In addition, as shown in FIG. 12a, the central axes A1 and A2 of the head receiving chamber and the rod receiving chamber are parallel in this case and the chambers are arranged such that the locking elements are accessible from the same side.

Figure 13:
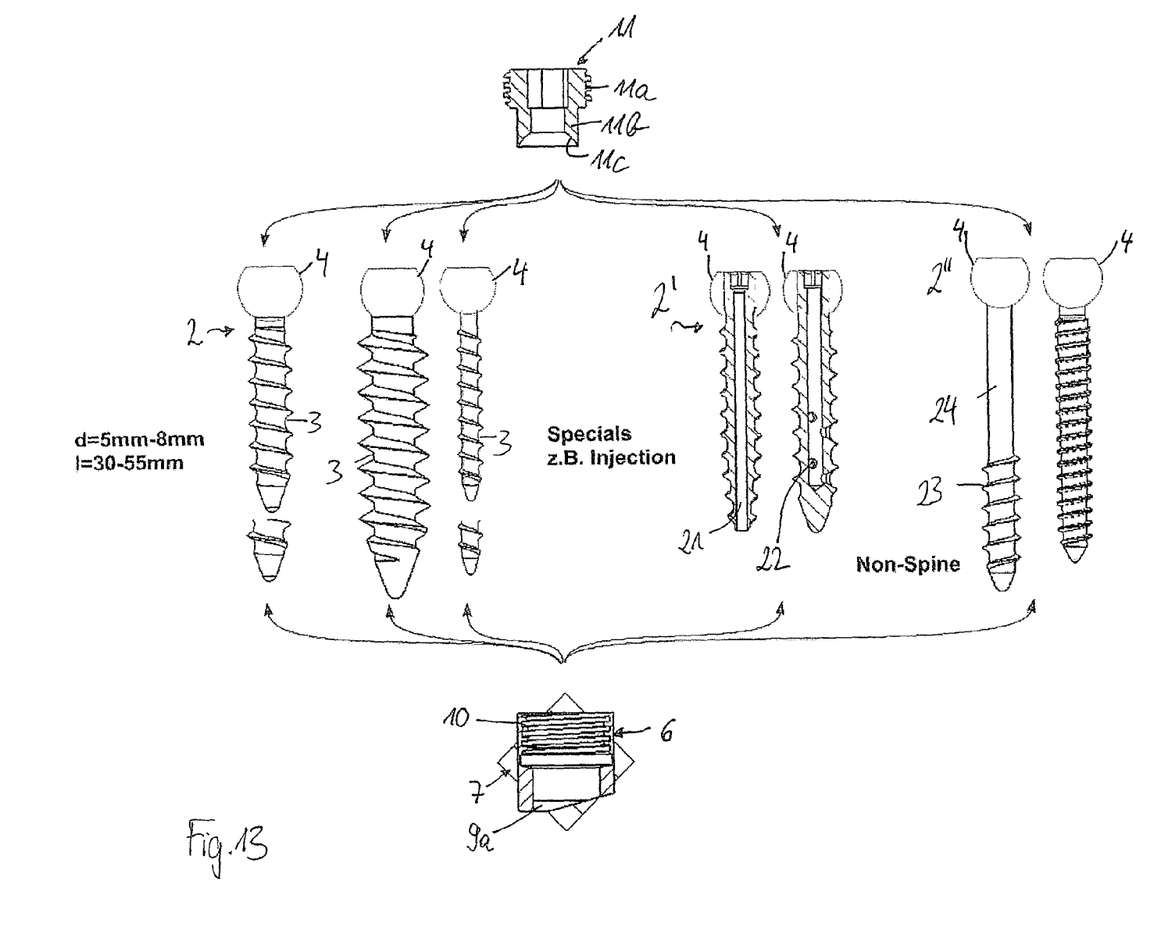
FIG. 13 shows some possible combinations of different bone anchoring elements with the receiving member and the locking element for locking the head.

FIG. 13 shows a sectional view of the first locking element 11 and a partial sectional view of the head receiving chamber 6 showing the through-hole 9 together with different screw elements. The screw element 2 as shown in the left part of FIG. 13 can have different shanks 3 with different lengths and diameters. The screw element 2' shown in the middle portion has a coaxial bore 21 extending therethrough from the first end to the tip, providing a channel for the introduction of bone cement or other substances. In another example, the bore 21 is closed at the tip of the shank and can have lateral openings 22 extending from the coaxial bore 21. In a further modification the screw element 2" can be a screw element for non-spine applications. The screw element 2" has a threaded portion 23 and a thread-free portion 24. Different screw members 2" with different threads can be provided. The features of the screw elements can be combined among each other. The head 4 of the different screw members 2, 2', 2" are all the same with respect to their outer shape and diameter so that they can be assembled with the receiver member described before and clamped with the same locking element 11.

In use, first the appropriate screw member and receiver member are selected. Thereafter, the screw member is inserted into the head receiving chamber of the receiver member. Thereafter the screw member is screwed into the bone. Typically, several screw members with receiver members are screwed one after the other into portions of adjacent vertebrae. Then, the angular position of the receiver member with respect to the screw member is adjusted and the first locking element 11 is inserted and tightened to clamp the head. Thus, the head is locked by a downward movement of the first locking element in the direction of the shank. Thereafter, the rod is inserted and is adjusted to the screw position. Thereafter, the rod is fixed by the second locking element. During adjustment of the positions of the rod and the head, it can be necessary to open the head and/or rod fixation again to further adjust the positions. Since the head fixation and the rod fixation are completely independent from each other, a convenient and precise adjustment is possible.

A second embodiment of the bone anchoring device will now be described with reference to FIGS. 14 to 24. The second embodiment differs from the first embodiment in the design of the receiver member 50. The screw member 2 is identical or similar to that of the first embodiment. Also, different screw members can be used as for the first embodiment. The receiver member 50 has a body having a substantially cuboid shape and the head receiving chamber and the rod receiving chamber are formed by portions of the cuboid body. The body has a first end 50a and a second end 50b, which can be defined as the short sides 51 of the cuboid. Between the first end 50a and the second end 50b, walls are defined between the long sides 52 of the cuboid. A central axis C extends through the center of the cuboid body and is parallel to the long sides 52. Approximately one half of the body, adjacent to the second end 50b, forms a head receiving chamber 60 that is constructed by means of a through-hole 90, the longitudinal axis 90a of which extends perpendicular to the central axis C of the cuboid body. The through-hole 90 is shaped similarly to the through-hole 9 of the first embodiment. The through-hole 90 includes, at one end, an opening 92 and an internal thread 100 adjacent to the opening 92 and in the through-hole 90. At the opposite end, the through-hole 90 includes a seat 91a for receiving the head 4 of the screw member 2 in a pivotable manner. At the first end 50a, an opening 75 to a U-shaped recess 74 is provided, where the U-shaped recess 74 forms a channel for receiving the rod 20. Adjacent to or near the first end 50a, an internal thread 150 is provided at the legs formed by the U-shaped recess. The central axis A2 of the internal thread 150 is coaxial with the central axis C of the body 50 and is perpendicular to the bore axis 90a of the through-hole 90. By means of this arrangement, the rod axis L and the screw axis S include an angle of approximately 90°±α, wherein α is the pivot angle that the screw can assume in the seat. Further, the screw axis S projects out of a plane that contains the rod axis L and the central axis C of the receiver member. This arrangement is particularly suitable for application in the lumbosacral region of the spine as shown in FIGS. 2 and 3.

Figure 14:
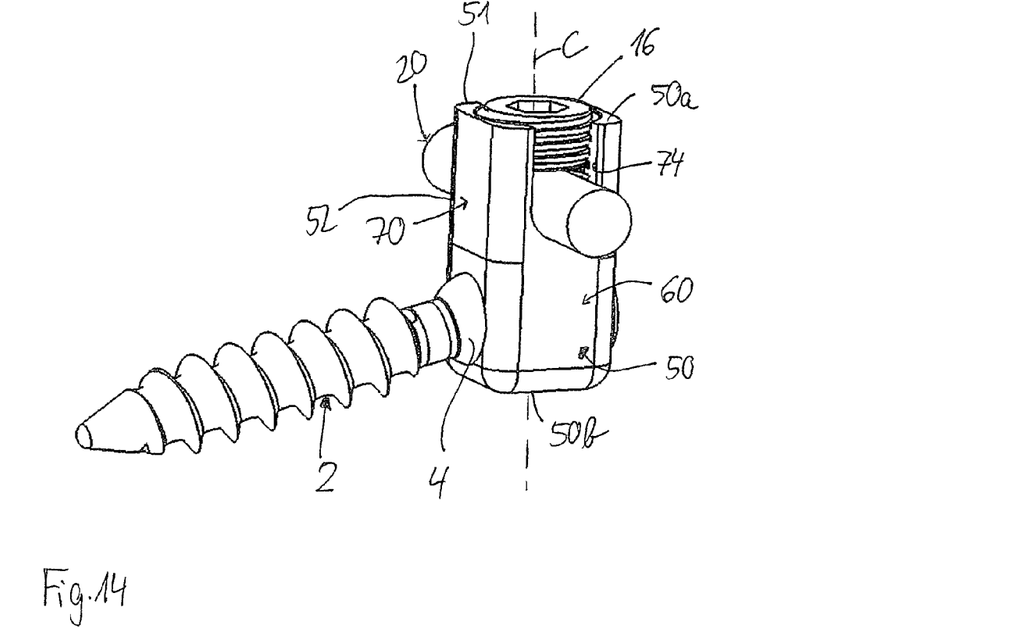
FIG. 14 shows a perspective view of a second embodiment of the bone anchoring device in an assembled state.
Figure 15:
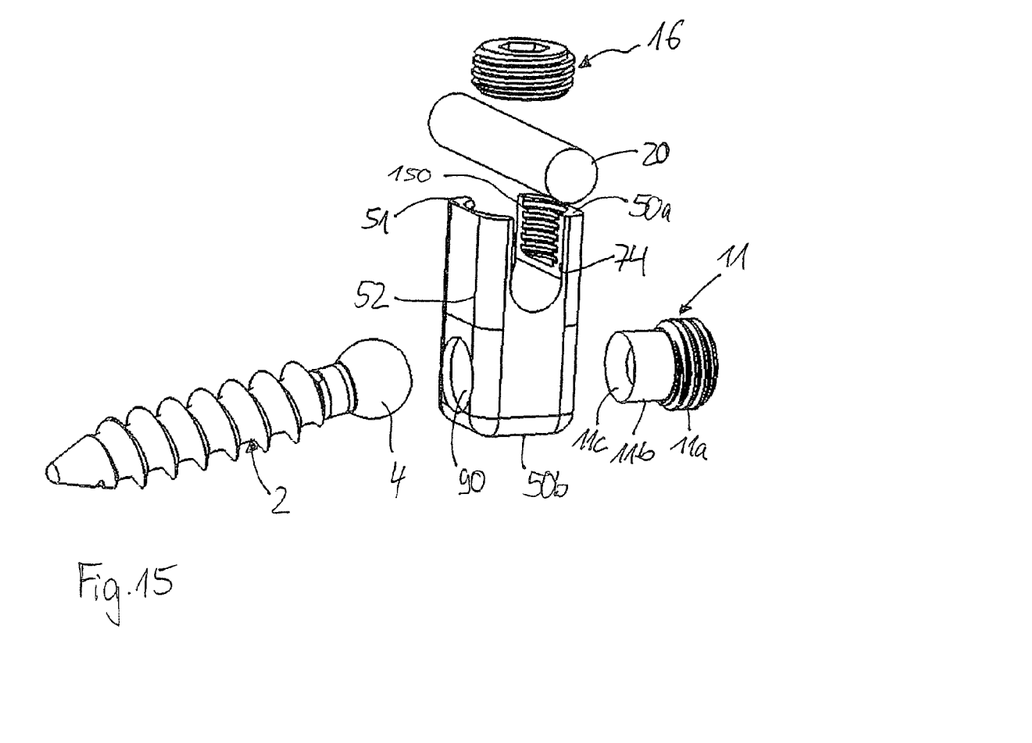
FIG. 15 shows a perspective exploded view of the bone anchoring device of FIG. 14.
Figure 16:
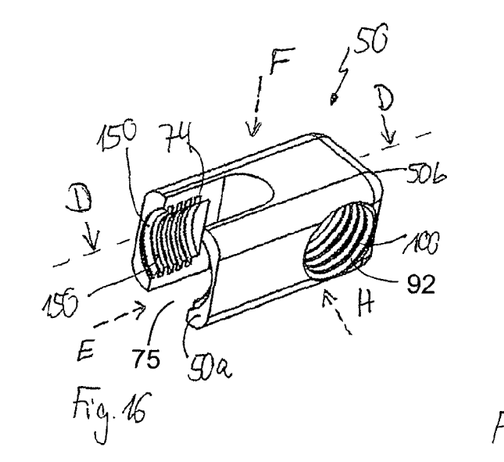
FIG. 16 shows a perspective view of the receiver member of the bone anchoring device according to the second embodiment.
Figure 17:
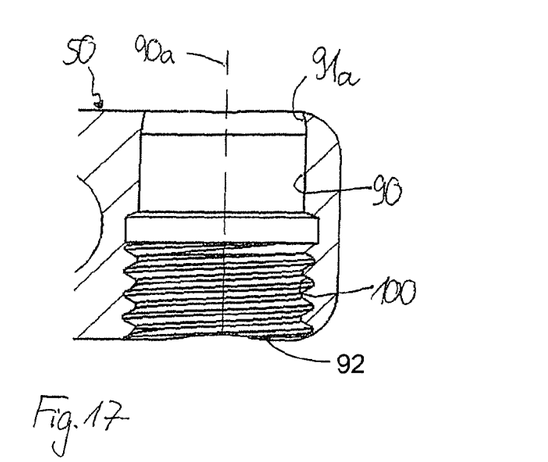
FIG. 17 shows an enlarged sectional view of the head receiving chamber of the receiver member of FIG. 16, the section being taken along line D-D in FIG. 16.
Figure 18:
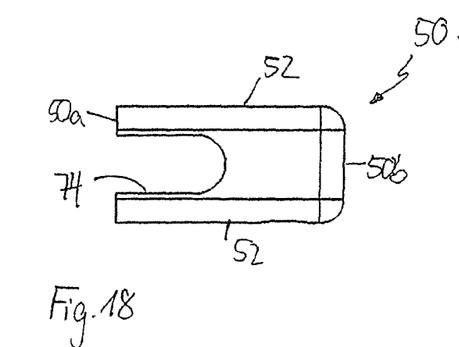
FIG. 18 shows a top view of the receiver member of FIG. 16 seen in the direction of arrow F.
Figure 19:
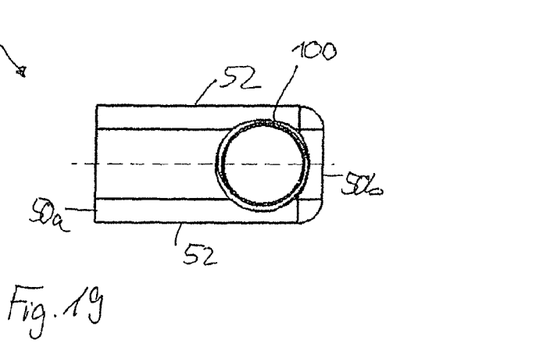
FIG. 19 shows a side view of the receiver member of FIG. 16 seen in the direction of arrow H.
Figure 20:
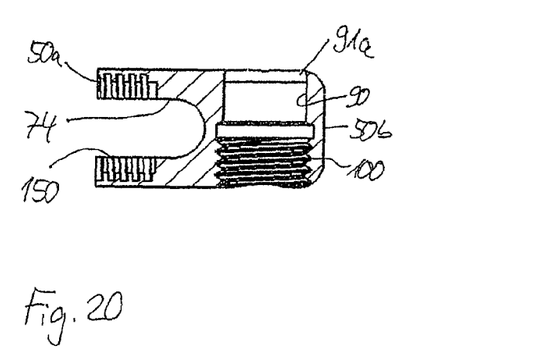
FIG. 20 shows a sectional view of the receiver member of FIG. 16 the section taken along line D-D.
Figure 21:
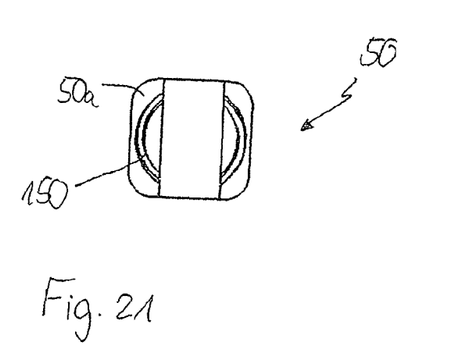
FIG. 21 shows a side view of the receiver member of FIG. 16 seen in the direction of arrow E.

The first locking element 11 and the second locking element 16 are the same as in the first embodiment.

The bone anchoring device of the second embodiment can also be used in other regions of the spinal column. If the screw member 2 is screwed into the pedicles, the bone anchoring device is a bone anchoring device with a lateral rod arrangement. Since the body 50 can be a compact design, a low-profile and low-cost bone anchoring device is provided.

Figure 22:
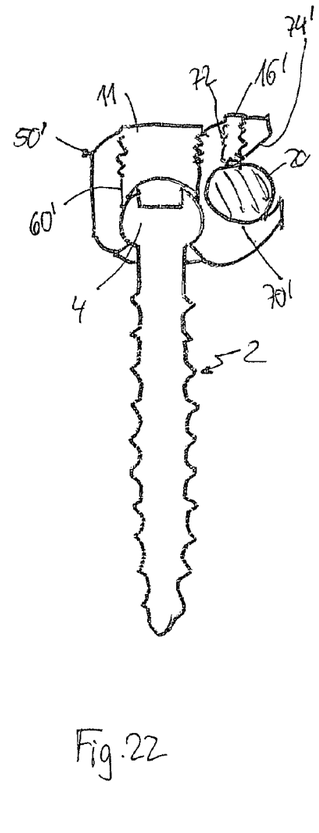
FIG. 22 shows a schematic view of a modified example of the second embodiment.
Figures 23, 24:
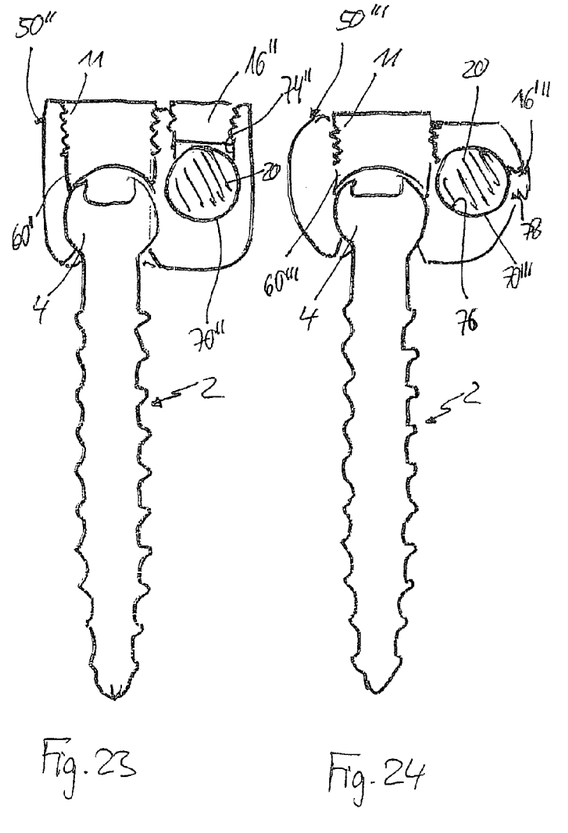
FIG. 23 shows a schematic view of a still further modified example of the second embodiment.
FIG. 24 shows a still further modified example of the second embodiment.

FIGS. 22 to 24 show further modifications of the second embodiment. All modifications have in common a compact body 50', 50", 50"', which has a head receiving chamber 60', 60", 60"' and a rod receiving chamber 70', 70", 70"', which are laterally separated from each other and can be accessed with two separate locking elements 11 and 16', 16", 16"'. In FIG. 22, the rod receiving chamber 70' is laterally arranged and has an inclined U-shaped recess 74' for introducing the rod 20 from the side and a locking element 16' in form of a set screw to be screwed in a threaded bore 72 extending from the top into the inclined U-shaped recess. This is a side-loading arrangement in which the locking elements 11 and 16' are accessible from the same side. In FIG. 23, the U-shaped recess 74" for the rod 20 extends from the same side as the threaded portion 100' of the through-hole 90' for the head 4. This embodiment is a top-loading embodiment, where the rod has a lateral arrangement and the locking elements for the head and the rod are accessible from the same side. FIG. 24 shows a further modification, where instead of a U-shaped recess, a through-hole 76 for the rod 20 is provided and the rod is secured by a set screw 16"' extending through a threaded bore 78.

The shape of the receiver member of the second embodiment is not limited to the shapes depicted in FIGS. 14-24. Common to all modifications is that the receiver member has a body with a compact shape. The head need not be spherically shaped, but can also have a tapered portion or another shape.

What is claimed is:

1. A bone anchoring device comprising:
   a bone anchoring element having a shank and a head;
   a receiver member for receiving the head of the bone anchoring element and for receiving a rod, wherein the receiver member has a first chamber for receiving the head therein, the head being pivotable in the first chamber, and a second chamber with a channel for receiving the rod;
   a first locking element configured to be secured to the first chamber, wherein the first locking element is a monolithic locking element; and
   a second locking element configured to be secured to the second chamber;
   wherein the first chamber has an opening to receive the first locking element and has a first engagement structure configured to cooperate with the first locking element and the second chamber has an opening to receive the second locking element and has a second engagement structure configured to cooperate with the second locking element;
   wherein the first chamber and the second chamber share a portion of a wall such that the portion of the wall forms both a part of the first chamber and a part of the second chamber on opposite sides thereof, and the portion of the wall further comprising both a part of the first engagement structure and a part of the second engagement structure on opposite sides thereof;
   wherein the first chamber and the second chamber are arranged in such a way that the head and the rod can be inserted and locked independently from each other; and
   wherein the head is fixed by applying pressure onto it via direct contact with the first locking element and wherein the rod is fixed by applying pressure onto it via the second locking element.

2. The bone anchoring device of claim 1, wherein the bone anchoring element is a monolithic bone anchoring element.

3. The bone anchoring device of claim 1, wherein the first locking element comprises a threaded portion to engage the first engagement structure of the first chamber and a pressure portion with a recess at a side facing the head to directly contact and distribute the pressure onto the head.

4. The bone anchoring device of claim 1, wherein the head has a spherically-shaped portion.

5. The bone anchoring device of claim 1, wherein the receiver member is a monolithic receiver member and wherein the first chamber comprises a through-hole with a seat at one end to engage and fix the head between the first locking element and the seat.

6. The bone anchoring device of claim 5, wherein the first engagement structure is a thread.

7. The bone anchoring device of claim 1, wherein the second chamber comprises a substantially U-shaped recess, wherein the rod is insertable through the open side of the substantially U-shaped recess.

8. The bone anchoring device of claim 1, wherein the second locking element is a monolithic locking element.

9. The bone anchoring device of claim 1, wherein the second locking element is a set screw.

10. The bone anchoring device of claim 1, further comprising a rod wherein the rod is configured to be received into the receiving member and is arranged laterally with respect to the anchoring element.

11. The bone anchoring device of claim 10, wherein the second locking element is configured to act directly onto the rod when secured to the second chamber with the rod in the second chamber.

12. The bone anchoring device of claim 1, wherein the first locking element and the second locking element are accessible from the same side.

13. The bone anchoring device of claim 1, wherein the receiver member has a top surface defining the opening to the first chamber and the opening to the second chamber; and wherein both the first locking member and the second locking member extend below the entire top surface.

14. The bone anchoring device of claim 13, wherein the top surface is planar.

15. A bone anchoring device comprising:
   a bone anchoring element having a shank and a head,
   a receiver member for receiving the head of the bone anchoring element and for receiving a rod, wherein the receiver member has a first chamber for receiving the head therein, the head being pivotable in the first chamber, and a second chamber with a channel for receiving the rod;
   a first locking element configured to be secured to the first chamber, wherein the first locking element is a monolithic locking element; and
   a second locking element configured to be secured to the second chamber;
   wherein the first chamber has an opening configured to receive the first locking element and has an engagement structure configured to cooperate with the first locking element;

wherein the second chamber has an opening configured to receive the second locking element and has an engagement structure configured to cooperate with the second locking element;

wherein the first locking element and the second locking element have central axes that are perpendicular to each other when the first and second locking elements are secured to the first and second chambers of the receiver member, respectively;

wherein the first chamber and the second chamber are arranged in such a way that the head and the rod can be inserted and locked independently from each other; and wherein the head is fixed by applying pressure onto it via direct contact with the first locking element and wherein the rod is fixed by applying pressure onto it via the second locking element.

16. The bone anchoring device of claim 15, wherein the first locking element and the second locking element are threaded around their respective central axes.

17. The bone anchoring device of claim 16, wherein the first locking element comprises a threaded portion to engage the engagement structure of the first chamber and a pressure portion with a recess at a side facing the head to directly contact and distribute the pressure onto the head.

18. The bone anchoring device of claim 17, wherein the receiver member is a monolithic receiver member and wherein the first chamber comprises a through-hole with a seat at one end to engage and fix the head between the first locking element and the seat.

19. A bone anchoring device comprising:
a bone anchoring element having a shank and a head;
a rod having a longitudinal rod axis;
a receiver member for receiving the head of the bone anchoring element and for receiving a rod, wherein the receiver member has a first chamber for receiving the head therein, the head being pivotable in the first chamber, and a second chamber with a channel for receiving the rod;

a first locking element configured to be secured to the first chamber, wherein the first locking element is a monolithic locking element; and a second locking element configured to be secured to the second chamber;

wherein the first chamber has an opening configured to receive the first locking element and has an engagement structure configured to cooperate with the first locking element;

wherein the second chamber has an opening configured to receive the second locking element and has an engagement structure configured to cooperate with the second locking element;

wherein the first locking element and the second locking element have central axes that are perpendicular to each other when the first and second locking elements are secured to the first and second chambers of the receiver member, respectively;

wherein the first chamber and the second chamber are arranged in such a way that the head and the rod can be inserted and locked independently from each other by the first and second locking elements, respectively;

wherein the head is fixed by applying pressure onto it via direct contact with the first locking element and wherein the rod is fixed by applying pressure onto it via the second locking element; and wherein the receiver member comprises a first pair of parallel sides and a second pair of parallel sides connecting the first pair of parallel sides, wherein the central axis of the first locking element is perpendicular to the first pair of parallel sides when secured to the first chamber and wherein the longitudinal axis of the rod is perpendicular to the second pair of parallel sides when secured in the second chamber.

\* \* \* \* \*